United States Patent [19]
Yoshida et al.

[11] Patent Number: 5,714,675
[45] Date of Patent: Feb. 3, 1998

[54] IMPACT TESTING AND PROCESSING APPARATUS ELECTROTHERMALLY ACCELERATING AND PROJECTING FLIER AGAINST SPECIMEN

[75] Inventors: Hiroo Yoshida, Tsukuba; Kazuo Uematsu; Masao Ochi, both of Yokohama, all of Japan

[73] Assignees: Director General of Agency of Industrial Science and Technology; Ishikawajima-Harima Jukogyo Kabushiki Kaisha, both of Tokyo-to, Japan

[21] Appl. No.: 761,149

[22] Filed: Dec. 6, 1996

[30] Foreign Application Priority Data

Feb. 29, 1996 [JP] Japan ................... 8-042797

[51] Int. Cl.⁶ ............... G01M 7/00; G01N 3/08; G01N 3/30; G01N 3/32
[52] U.S. Cl. ................ 73/12.04; 73/863.22
[58] Field of Search ................ 73/12.01, 12.02, 73/12.04, 12.05, 12.06, 86.22

[56] References Cited

U.S. PATENT DOCUMENTS

| | | | |
|---|---|---|---|
| 4,696,182 | 9/1987 | Meir | 73/12.05 |
| 4,866,929 | 9/1989 | Knowles et al. | 60/202 |
| 4,989,462 | 2/1991 | Davis et al. | 73/12.01 |
| 5,528,974 | 6/1996 | Yoshida et al. | 89/14.6 |

FOREIGN PATENT DOCUMENTS

| | | |
|---|---|---|
| 6-66674 | 3/1994 | Japan . |
| 6-323951 | 11/1994 | Japan . |

*Primary Examiner*—Richard Chilcot
*Assistant Examiner*—Max H. Noori
*Attorney, Agent, or Firm*—Oblon, Spivak, McClelland, Maier & Neustadt, P.C.

[57] ABSTRACT

A flier launched from an electrothermal accelerator 2 is collided against a specimen 53 retained in a sealed specimen receptacle 36, so that impact testing or perforation processing can be effected without disturbing collision environments such as temperature and atmosphere.

4 Claims, 8 Drawing Sheets

IMPACT TESTING AND PROCESSING APPARATUS ELECTROTHERMALLY ACCELERATING AND PROJECTING FLIER AGAINST SPECIMEN

BACKGROUND OF THE INVENTION

The present invention relates to an impact testing and processing apparatus.

Research and development activities have been made on use of new materials such as ceramics for turbine blades or the like. Ceramics are highly heat-resistant, but are relatively fragile. It is, therefore, important to investigate how a turbine blade made of ceramics and placed in high-temperature combustion gas can endure collision of various particles such as combustion products and/or foreign matters in the combustion gas. On the basis of such investigation, it is necessary to determine a guideline for safety designing of ceramic turbine blade and to establish a technique for impact testing and evaluation of the material. Apart from the above, there are demands for processing of the material such as perforation of a specimen (material to be impacted) through high-speed collision of a minute particle against the specimen.

Conventionally, impact testing or processing as described above has been performed in such a manner that a minute flier or flying object simulating the above-mentioned particle is loaded on a front surface of an auxiliary acceleration jig which is a so-called "sabot" and the flier is launched and accelerated together with the jig toward a specimen by a gas gun or gunpowder gun. Only the jig is stopped just before the specimen by a stopper to separate the flier from the jig. Then, the separated flier is collided against the specimen. Thus, the testing or processing is carried out.

However, in the above-mentioned impact testing and processing system using the gas gun or gunpowder gun, collision environments such as temperature and atmosphere around the specimen are disturbed by the gas used for the acceleration of the auxiliary acceleration jig and for separated collision of the flier against the specimen. As a result, testing or processing conditions become deviant, which causes difficulty in obtaining accurate results.

The present invention was made to solve the above and other problems encountered in the prior art and has its object to provide an impact testing and processing apparatus capable of colliding a flier against material to be impacted without disturbing collision environments such as temperature and atmosphere.

BRIEF SUMMARY OF THE INVENTION

To attain the above objects, an impact testing and processing apparatus according to the present invention comprises an electrothermal accelerator, said accelerator comprising an anode cylinder for accommodation of a flier, an insulating cylinder having therein an evaporation space communicated with a rear end of said anode cylinder, a cathode for blocking a side of the evaporation space away from to the anode cylinder and a high-voltage heavy current source for connection between the anode cylinder and cathode, said accelerator being mounted on a sealed specimen container which accommodates and retains a specimen.

In this case, the accelerator may be mounted on the specimen container through an angle adjustment mechanism which can change an incident angle of the flier to the specimen.

The specimen container may have a receptacle capable of receiving a liquid specimen.

The accelerator may further comprise an auxiliary acceleration jig for supporting the flier and a stopper on a forward end of the accelerator for stopping the jig and separating and projecting the flier from the jig and out of the accelerator.

The impact testing and processing apparatus as described above will attain the following.

When electric current is supplied between the anode cylinder and cathode by the high-voltage heavy current source, electric discharge is generated between the two electrodes; and heat of the electric discharge evaporates the insulating cylinder positioned between the two electrodes. By pressure of high-temperature and high-pressure gas thus generated, the flier is accelerated and projected through the forward end of the accelerator.

In this case, the flier may be supported by the auxiliary acceleration jig; and the jig may be stopped by the stopper on the forward end of the accelerator to separate the flier from the jig for projection of the flier out of the accelerator. As a result, the flier in the form of minute particle can be accelerated.

The electrothermal accelerator utilizes the pressure of the instantaneously generated gas of high temperature and high pressure. The gas generated is very low in volume and its influence on the atmosphere is negligible.

The flier projected out of the accelerator is collided against the specimen, which is held in the sealed specimen container, so that impact testing or perforation of the specimen can be performed.

In this case, the angle adjusting mechanism may be used to change an angle between the specimen container and accelerator to change an incident angle of the flier to the specimen.

Since the direction of the accelerator can be changed by the angle adjusting mechanism, if a receptacle capable of receiving a liquid specimen is used as the specimen container and the flier is collided from above against the specimen, impact testing on the liquid specimen can be performed.

Since the direction of the accelerator can be changed by the angle adjusting mechanism, if the specimen is directed downward and the flier in the form of power charged in the auxiliary acceleration jig is collided from below against the specimen, impact testing or processing can be performed, using the flier in the form of powder.

DETAILED DESCRIPTION OF THE PREFERRED EMBODIMENTS

FIGS. 1 to 4 represent a first embodiment of the present invention.

An electrothermal accelerator 2 is used as means for accelerating a flier or flying object 1.

Figure 3:
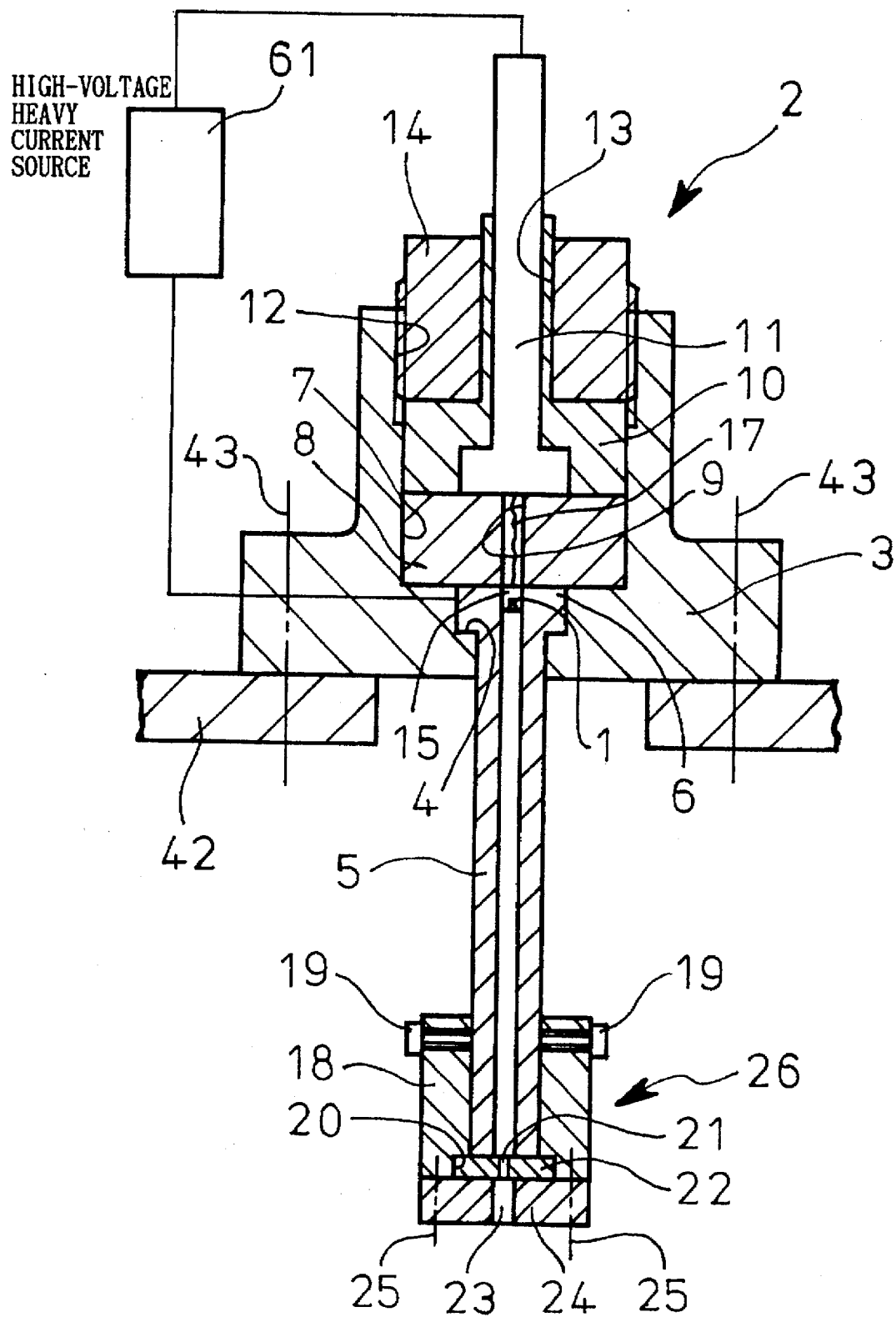
FIG. 3 is a sectional side elevation of the electrothermal accelerator shown in FIG. 1.

The electrothermal accelerator 2 comprises, as shown in FIG. 3, an electrothermal accelerator main body 3 generally in the form of cylinder with its forward end (the lower end in the figure) closed. The accelerator main body 3 is formed, at its forward end wall, with a stepped axial opening 4 with which a flange 6 on a rear end of an anode cylinder 5 is engaged. The accelerator main body 3 has an inner accommodation space 7 in which an insulating cylinder 8 is inserted and arranged in such manner that an evaporation space 9 in the cylinder 8 is communicated with a rear end of the anode cylinder 5. In the accommodation space 7 and behind a rear end of the insulating cylinder 8, a substantially rod-like cathode 11 with its periphery protected by an insulator 10 is inserted and arranged to block the evaporation space 9. A holding screw 14 with a bore 13 fitted over and supporting the cathode 11 and insulator 10 is meshed with an inner thread 12 on the rear end of the main body 3, which defines the accommodation space 7, so as to integrally fix these components. A high-voltage heavy current source 61 is connected between the anode cylinder 5 and cathode 11.

In the figures, reference numeral 15 represents an auxiliary acceleration jig such as so-called "sabot" which is placed in the anode cylinder 5; 16, a recess on the jig 15 into which the flier 1 is inserted; and 17, an auxiliary conducting member such as aluminum or the like metal foil or fuse arranged in the evaporation space 9 of the insulating cylinder 8 to electrically interconnect the anode cylinder 5 and cathode 11.

A sabot stopper main body 18 in the form of cylinder is removably mounted on a forward end of the anode cylinder 5 by mounting screws 19. The sabot stopper main body 18 is formed, at its forward end, with a holding step 20 in which a sabot stopping plate 22 with a small hole 21 for sabot separation and of the same diameter as that of the recess 16 of the jig 15 is fitted in such manner that the small hole 21 is aligned with an axis of the anode cylinder 5. Further, from outside of the sabot-stopping plate 22, a pressure plate 24 having a through hole 23 larger in diameter than and communicated with the small hole 21 is mounted on the forward end of the sabot stopper main body 18 by set screws 25. Thus, a sabot stopper 26 is provided.

Figure 1:
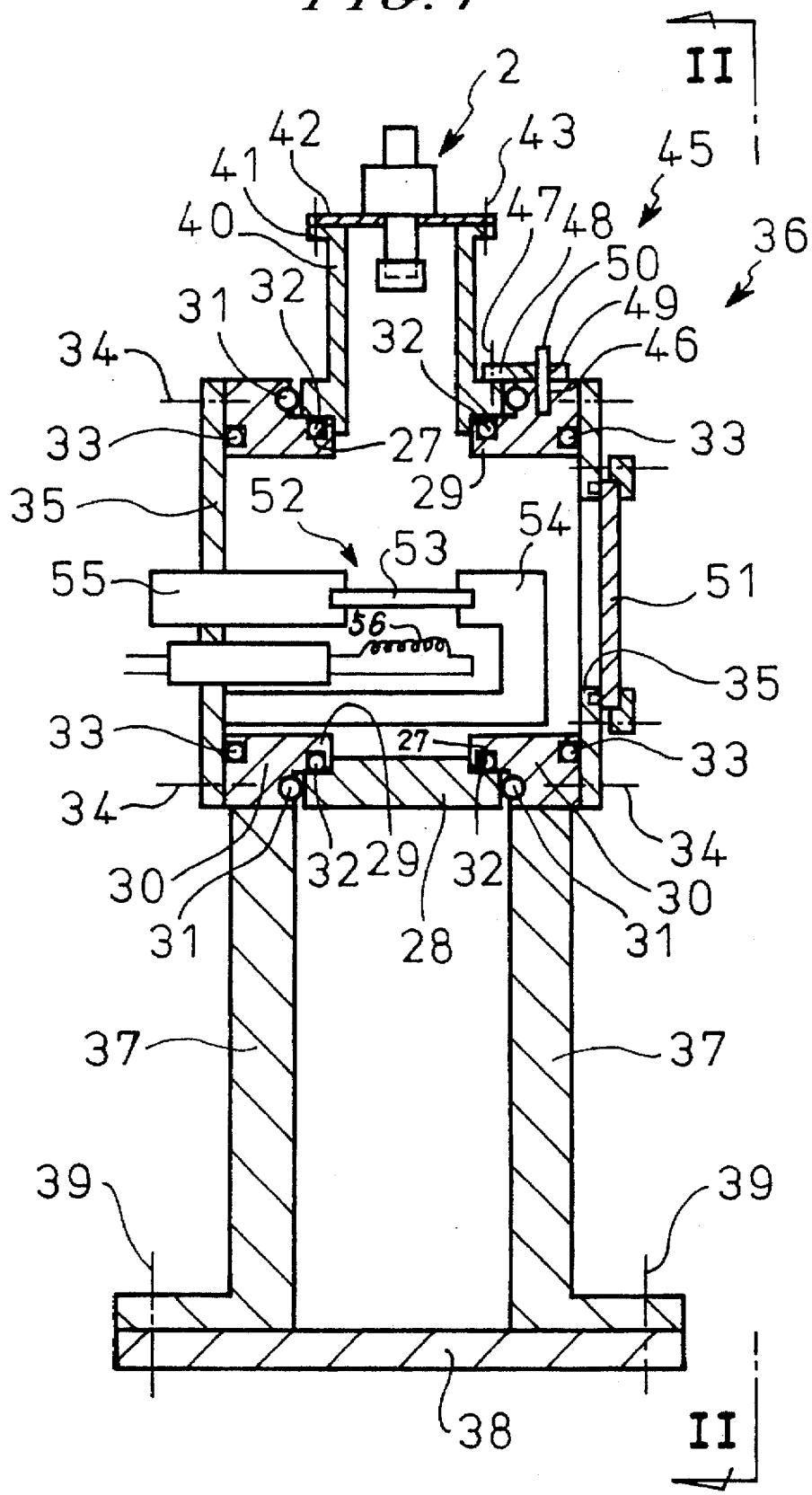
FIG. 1 is a sectional side elevation of a first embodiment of the present invention.
Figure 2:
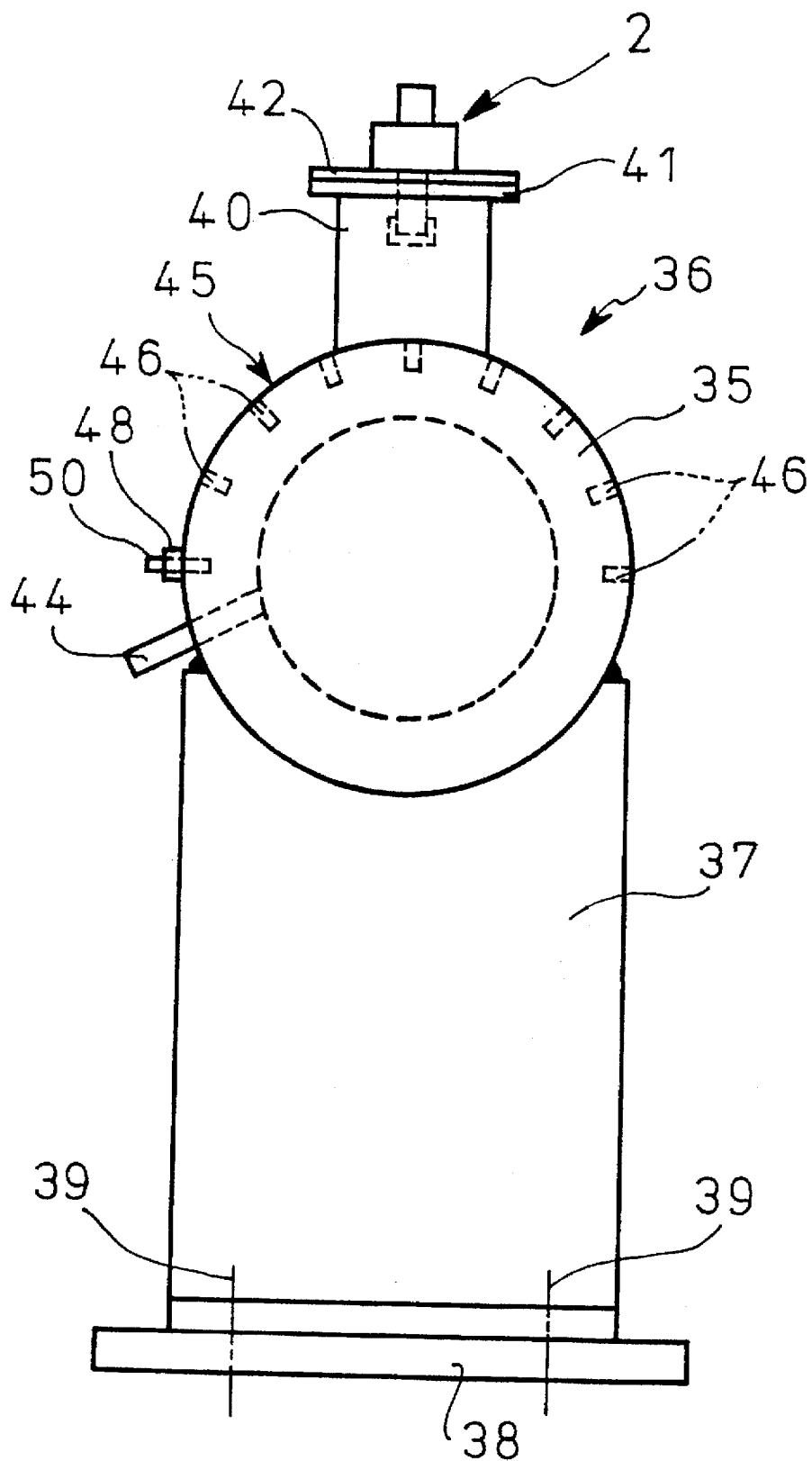
FIG. 2 is a view looking in the direction of arrows II in FIG. 1, although the pin support member is mounted at a different position.

On the other hand, as shown in FIGS. 1 and 2, provided is a cylindrical container piece 28 having an annular recess 27 on each of its opposite end surfaces. Further provided are two cylindrical container pieces 30 each having, at its one end surface, with an annular projection 29 which is engageable with the corresponding annular recess 27 of the container piece 28. The container pieces 30 are engaged, through bearings 31 and seals 32, with the container piece 28 in such a manner that they are relatively rotatable around a horizontal axis. A shut-off plate 35 is removably mounted, through a seal 33 and bolts 34, on the other end surface of each of the container pieces 30 away from the container piece 28. Thus, a specimen container 36 is provided. Each of the container pieces 30 is fixed to an upper end of a leg 37 by welding and the legs 37 are fixed at their lower ends to a base plate 38 by bolts 39, so that the specimen container 36 can stand by itself.

An acceleration cylinder 40 is protruded radially from the intermediate container piece 28 (and, in the figures, is at its uppermost position). The acceleration cylinder 40 has at its one end (upper end in the figures) a flange 41 on which the above-mentioned accelerator 2 is mounted through a mounting plate 42 and bolts 43 so as to be directed toward an axis of the specimen container 36 One of the container pieces 30 has a vacuum exhaust port 44 to which a vacuum pump (not shown) or an atmosphere gas supply source (not shown) is connected.

An angle adjusting mechanism 45 is arranged between the intermediate container piece 28 and one of the container pieces 30 and comprises, for example, a plurality of radially extending and mutually equiangularly spaced pin holes 46 on a peripheral surface of the container piece 30, a pin support member 48 mounted at an arbitrary position on the intermediate container piece 28 by a bolt 47, and a stop pin 50 inserted through a pin hole 49 on the member 48 and one of the pin holes 46 on the container piece 30 aligned with the pin hole 49.

For facilitation in drawing, FIG. 1 shows a case where the pin support member 48 is mounted on the container piece 28 at a position of the acceleration cylinder 40 being protruded. In this case, when the acceleration cylinder 40 is rotated or displaced to its lowermost position near the base plate 38, the pin support member 48 must be re-mounted on an upper portion of the container piece 28 which is away from the acceleration cylinder 40 so as to prevent interference with the legs 37. This advantageously prevents the stop pin 50 from dropping off due to its gravity. Alternatively, as shown in FIG. 2, the pin support member 48 may be mounted on the container piece 28 at a position deviated by 90 degrees from the position of the acceleration cylinder 40 being protruded; then, the pin support member 48 does not interfere with the leg 37 even when the container piece 28 is rotated or displaced within the range of 180 degrees between its uppermost and lowermost positions.

One of the shut-off plates 35 has an observation window 51 and the other of the plates 35 has a specimen support mechanism 52 to support a specimen 53 (material to be impacted) on the axis of the specimen container 36. The specimen support mechanism 52 may be replaced with any type of support mechanism depending upon intended use.

In this first embodiment, the specimen support mechanism 52 may comprise, for example, a fixed clamp 54 which grasps one end of the solid specimen 53 such as ceramic turbine blade and a movable clamp 55 in the form of cylinder or ball screw which grasps the other end of the specimen 53 and gives tensile stress to the specimen 53. In this case, if required, a heating device 56 such as a heater to heat the specimen 53 may be provided.

Next, mode of operation of the first embodiment will be described.

Figure 4:
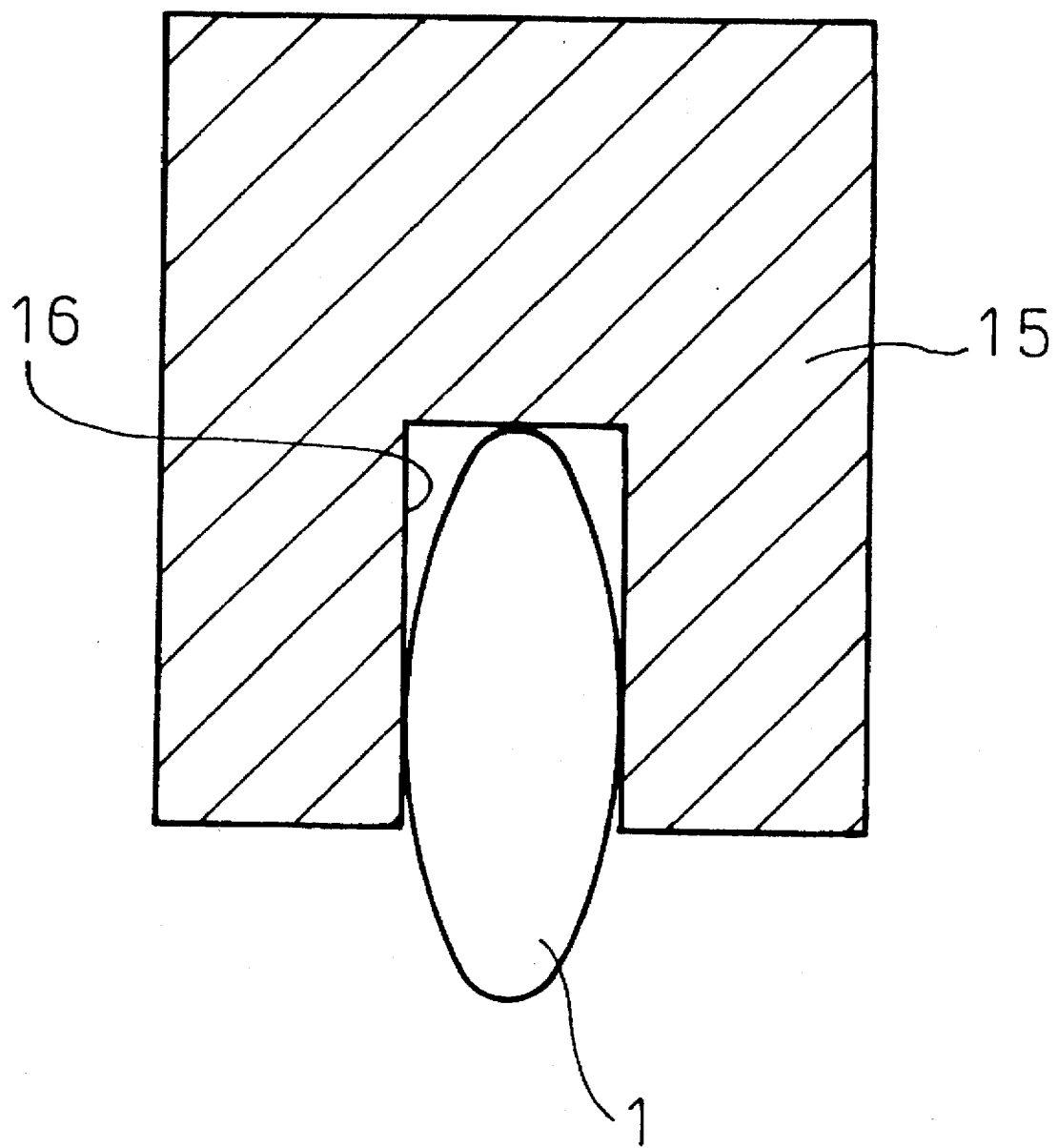
FIG. 4 is a sectional side elevation of the auxiliary acceleration jig shown in FIG. 1.

First, the electrothermal accelerator 2 is operated as follows:

Specifically, as shown in FIGS. 3 and 4, the flier 1 in the form of particle is loaded in the recess 16 on the acceleration supplementary jig 15 such as "sabot" and the jig 15 is placed in the anode cylinder 5. Then, electric current is supplied between the anode cylinder 5 and cathode 11 by the high-voltage heavy current source 61 to generate electric discharge within the evaporation space 9 of the insulating cylinder 8 positioned between the anode cylinder 5 and cathode 11. Heat caused by the electric discharge evaporates the insulating cylinder 8 in the evaporation space 9 to generate high-temperature and high-pressure gas. By the pressure of this gas, the flier 1 is accelerated and launched together with the acceleration supplementary jig 15.

Before the electric discharge is generated, the connection between the anode cylinder 5 and the cathode 11 is shorted in advance by the auxiliary conducting member 17 such as aluminum or the like metal foil or fuse so as to generate the electric discharge in stable and reliable manner. The auxiliary conducting member 17 used is evaporated instantaneously by the electric discharge.

When reaching the forward end of the anode cylinder 5, the accelerated acceleration supplementary jig 15 is stopped by the sabot stopping plate 22 of the sabot stopper 26 on the forward end of the cylinder 5. The flier 1 is separated from the stopped jig 15 by inertia and only the flier 1 passes through the small hole 21 and is projected through the forward end of the anode cylinder 5. In this case, the time required from the starting of electric discharge to the discharge or projection of the flier 1 out of the accelerator 2 is approximately on the order of hundreds of microseconds.

It is needles to say that the flier 1 of the same diameter as that of the acceleration supplementary jig 15 may be projected when the sabot stopper 26 is removed and that the flier 1 of any size may be projected by changing the size of the small hole 21 of the sabot stopping plate 22.

The electrothermal accelerator 2 as described above, which accelerates the flier 1 to a required speed, is of small size (15 cm or so in total length) in comparison with the conventional gas or gunpowder gun used.

The accelerator 2 accelerates the flier I by pressure of the instantaneously generated gas of high temperature and high pressure and the gas is very little in volume and its influence on the collision environments is substantially negligible.

On the other hand, in the specimen container 36, the solid specimen 53 such as ceramic turbine blade is grasped by the fixed clamp 54 and stress-applying movable clamp 55; and the shut-off plates 35 are mounted on the corresponding container pieces 30 by the bolts 34 and the specimen container 36 is sealed. The vacuum pump (not shown) is operated to evacuate the specimen container 36 via the vacuum exhaust port 44; or, atmospheric gas is introduced into the specimen container 36 from the atmosphere gas supply source (not shown), so that the interior of the specimen container 36 is tuned to any atmosphere as desired. If necessary, the stress-applying movable clamp 55 is caused to apply tensile stress on the specimen 53 and/or the specimen 53 is heated to a predetermined level of temperature by the heating device 56.

Under such condition, the flier 1 projected from the accelerator 2 is collided against the specimen 53 and impact testing for the flier 1 and the specimen 53 is carried out. Alternatively, processing such as perforation is carried out on the specimen 53. How the testing or processing is performed can be observed though the observation window 51.

As described above, according to the present invention, total height of the apparatus can be reduced to 1 meter or so since the small size accelerator 2 is used to accelerate the flier 1; and impact testing and processing may be carried out in easier manner on desk-top basis. Also, influence of gas used for acceleration is negligible since the electrothermal accelerator 2 is used.

The apparatus according to the present invention may be operated in diversified manner as described below since the specimen container 36 has the angle adjusting mechanism 45.

Specifically, the intermediate container piece 28 of the specimen container 36 may be rotated or displaced with respect to the container pieces 30 on both sides via the bearings 31 with the stop pin 50 removed and then, with the pin hole 49 of the pin support member 48 on the intermediate container piece 28 being aligned with an arbitrary pin hole 46 of the container piece 30, the stop pin 50 is inserted through the two holes 49 and 46. In this manner, the acceleration cylinder 40 may be displaced from its uppermost position as shown in FIGS. 1 and 2 where the cylinder 40 is perpendicular to the specimen 53 to any tilted position where the cylinder is tilted with respect to the vertical, which facilitates impact testing or processing with different incident angles of the flier 1 to the specimen 53.

Figure 5:
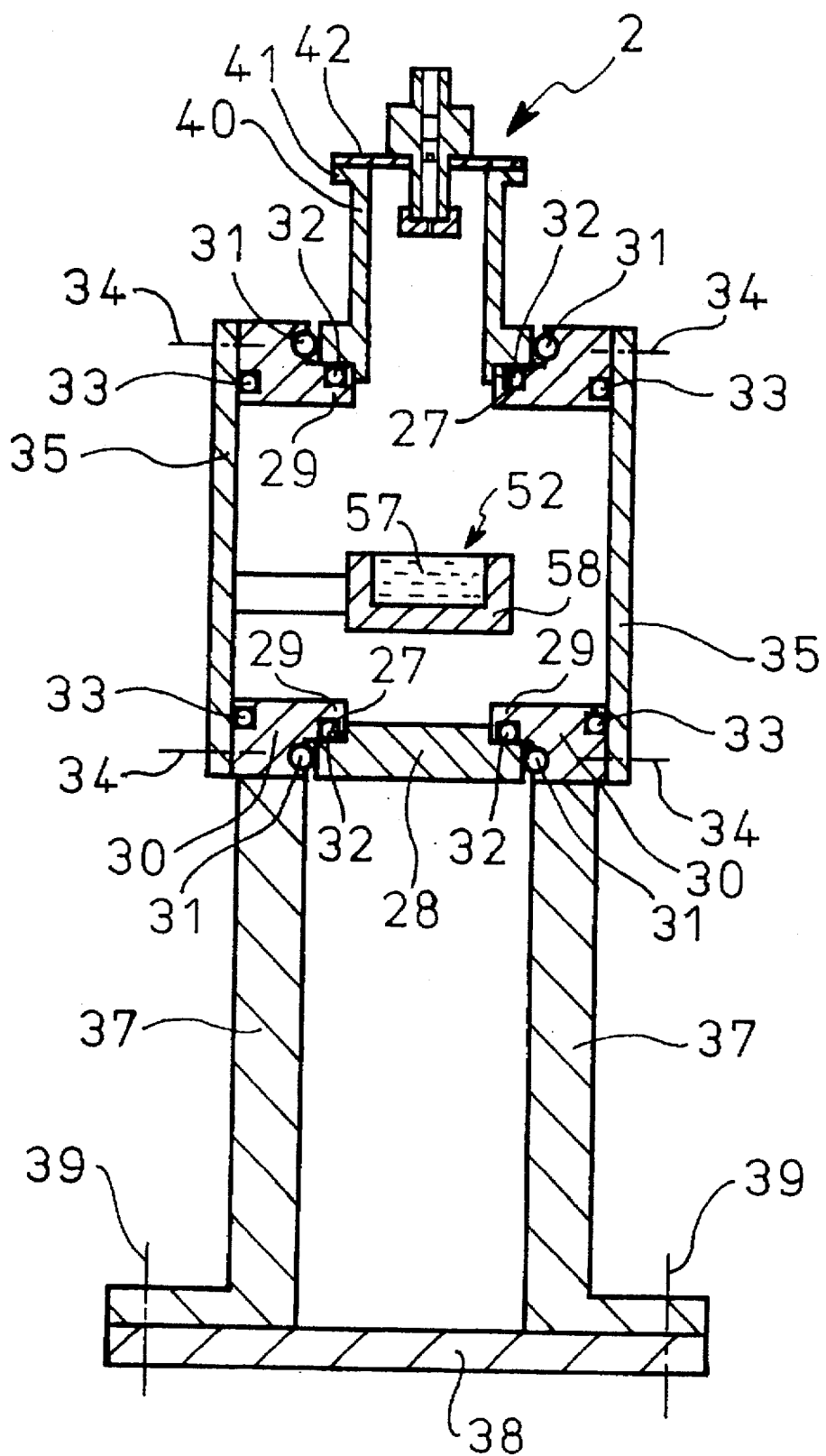
FIG. 5 is a sectional side elevation of a second embodiment of the present invention.

FIG. 5 shows a second embodiment of the present invention in which a receptacle 58 capable of receiving a liquid specimen 57 is mounted, as the specimen support mechanism 52, on one of the shut-off plates 35.

Since the angle of the accelerator 2 can be adjusted as mentioned above by the angle adjusting mechanism 45, by merely providing the shut-off plate 35 having the specimen support mechanism 52 in the form of the receptacle 58 capable of receiving the liquid specimen 57 and colliding the flier 1 from above against the specimen 57, impact testing of the flier 1 against the liquid specimen 57 can be carried out.

Except these, the second embodiment has the same arrangement as that of the above-mentioned first embodiment and can attain similar operations and effects.

Figure 6:
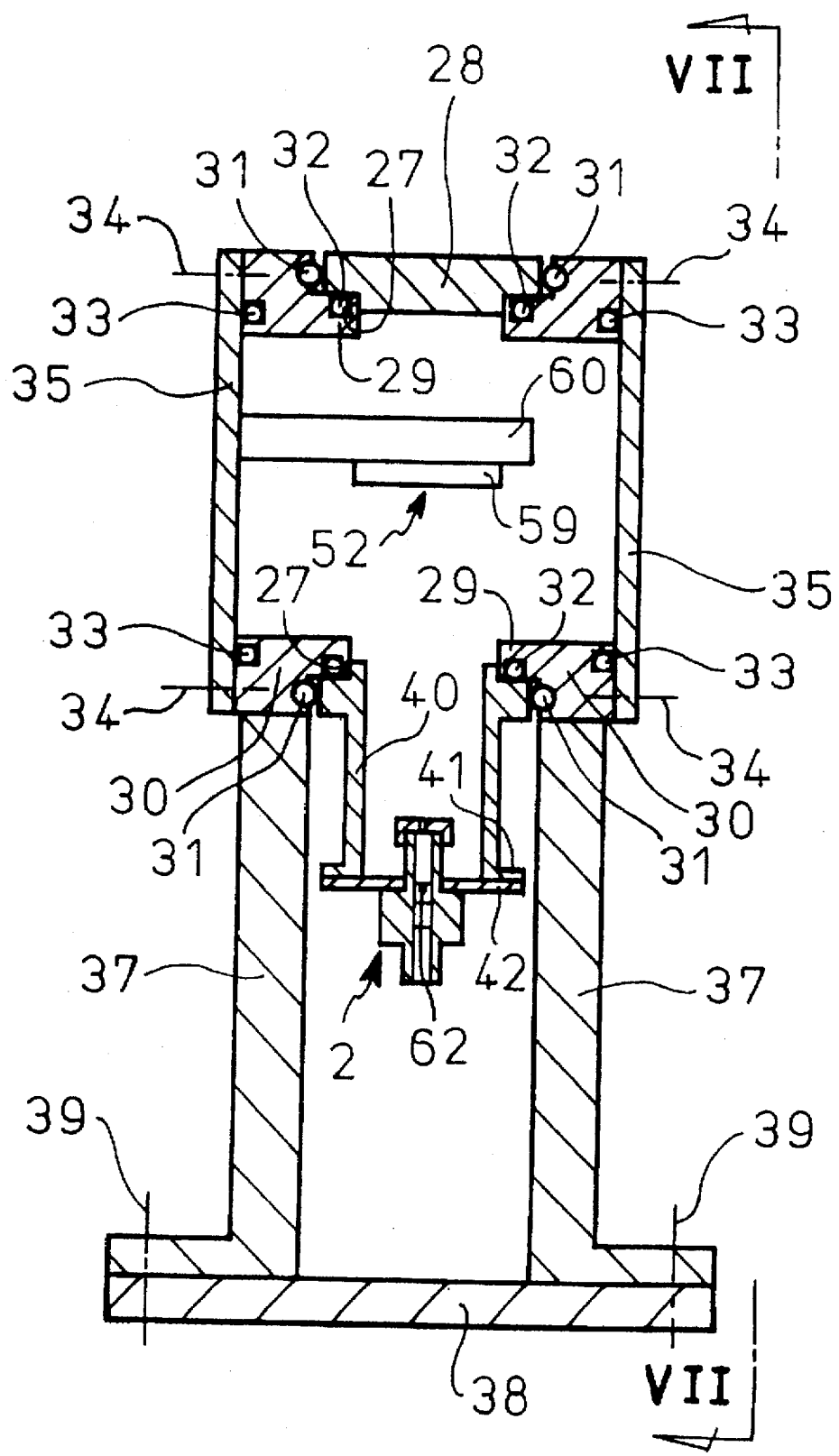
FIG. 6 is a sectional side elevation of a third embodiment of the present invention.
Figure 7:
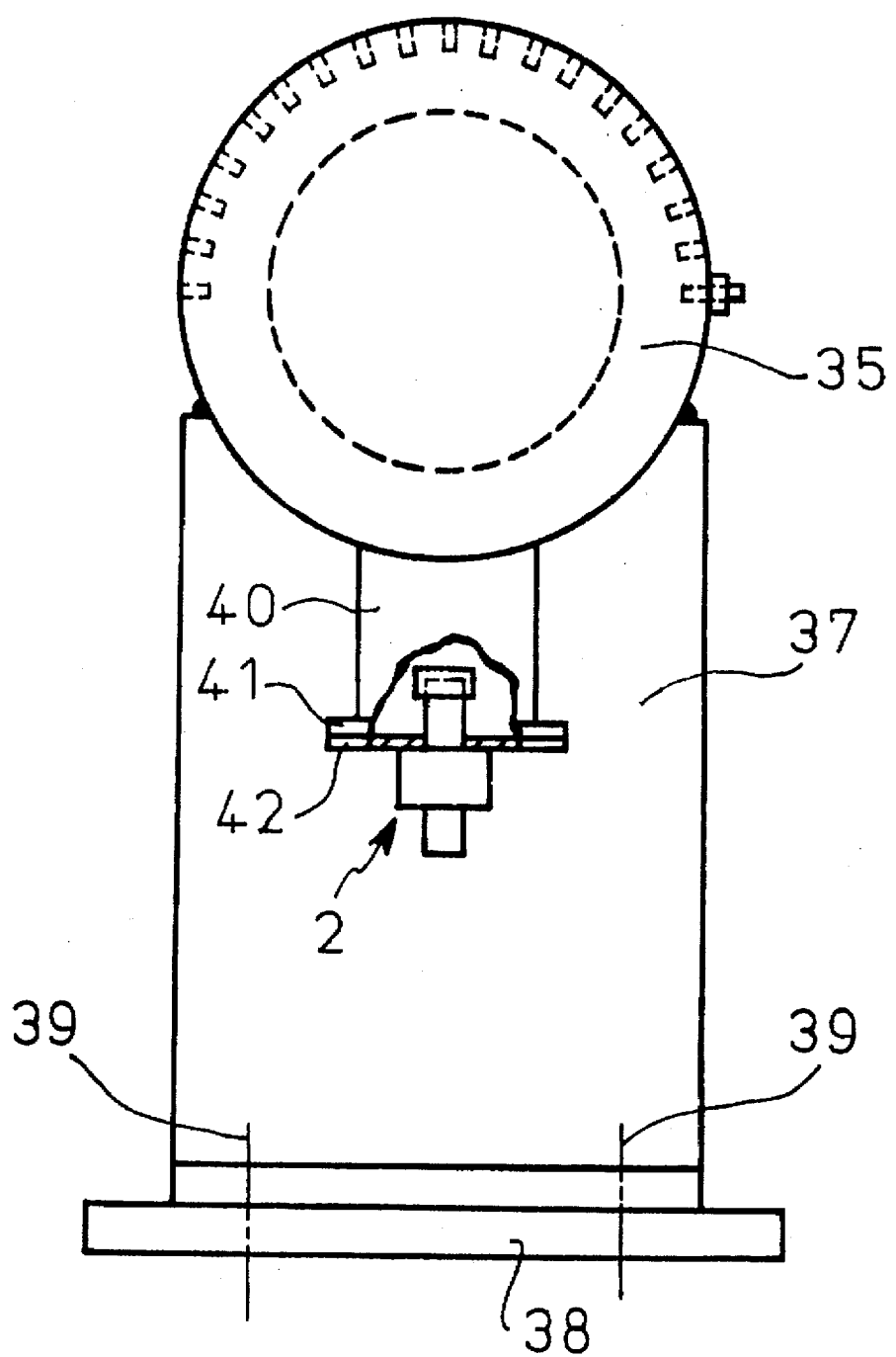
FIG. 7 is a view looking in the direction of arrows VII in FIG. 6.
Figure 8:
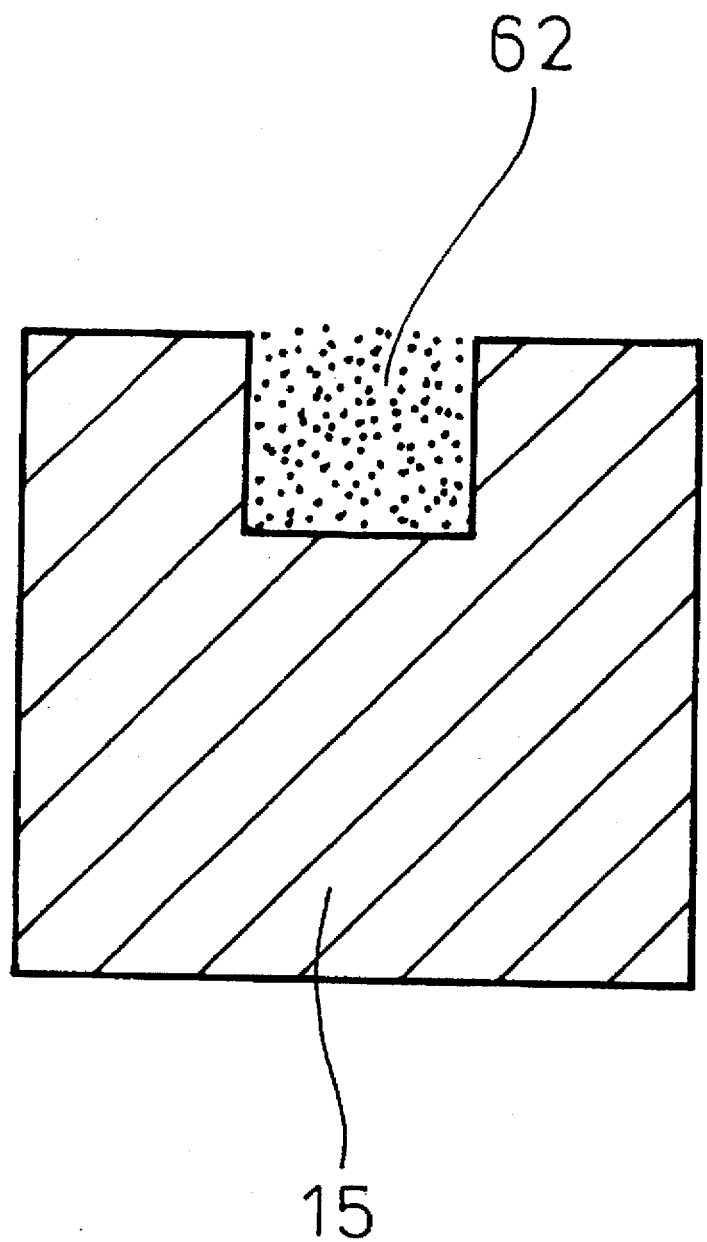
FIG. 8 is a sectional side elevation of the auxiliary acceleration jig shown in FIG. 6.

FIGS. 6 to 8 represent a third embodiment of the present invention in which the electrothermal accelerator 2 is directed upward by the angle adjusting mechanism 45 and flier 62 in the form of powder or liquid is filled in the recess 16 of the acceleration supplementary jig 15 of the accelerator 2.

The specimen support mechanism 52 used is of a simplified structure which comprises a specimen holding member 60 to merely hold the solid specimen 59 directed downward. Alternatively, the same specimen support mechanism 52 as shown in FIGS. 1 and 2 may be used.

In this third embodiment, the acceleration cylinder 40 is positioned at its lowermost position by the angle adjusting mechanism 45, and the flier 62 in the form of powder or liquid is filled in the recess 16 of the upwardly directed acceleration supplementary jig 15. By colliding the flier 62 from below against the specimen 59, impact testing or processing can be performed using the flier 62 in the form of powder or liquid.

Except these, the third embodiment has the same arrangement as that of the above-mentioned first and second embodiments and can attain similar operations and effects.

It is to be understood that the present invention is not limited to the above embodiments and that various changes and modifications may be made without departing from the scope and the spirit of the present invention. For example, the specimen container 36 and the angle adjusting mechanism 45 may be designed in any structures.

Instead of changing the tilting of the accelerator 2 by the angle adjusting mechanism 45, the container piece 30 may be mounted in peripherally different phase to the shut-off plate 35, thereby variously tilting the specimen support mechanism 52 supported by the container piece 30 and changing the incident angle of the flier 1 to the specimen 53.

As described above, the present invention can attain a superb effect of colliding a flier against material to be impacted without disturbing collision environments such as temperature and atmosphere.

What is claimed is:

1. An impact testing and processing apparatus comprising:

a sealed specimen container which accommodates and retains a specimen;

an electrothermal accelerator which accelerates and projects a flier from a forward end of said accelerator so as to collide the flier against the specimen, comprising, an anode cylinder which has a rear end and accommodates the flier, an insulating cylinder including an evaporation space having a rear end, and a forward end in communication with the rear end of said anode cylinder, a cathode which blocks the rear end of the evaporation space, and a high-voltage heavy current source electrically connected to the anode cylinder and the cathode; and an angle adjustment mechanism through which said accelerator is mounted on said specimen container and by which an incident angle of the flier to the specimen can be changed.

2. The apparatus according to claim 1, wherein said specimen container has a receptacle capable of receiving a liquid specimen.

3. The apparatus according to claim 1, wherein said accelerator further comprises, an auxiliary acceleration jig which supports the flier and is accelerated together with the flier, and a stopper provided at the forward end of the accelerator, said stopper stopping the accelerated jig so as to separate the flier from the jig and project the flier from the accelerator.

4. The apparatus according to claim 2, wherein said accelerator further comprises, an auxiliary acceleration jig which supports the flier and is accelerated together with the flier, and a stopper provided at the forward end of the accelerator, said stopper stopping the accelerated jig so as to separate the flier from the jig and project the flier from the accelerator.

* * * * *